(12) United States Patent
Strauss

(10) Patent No.: US 6,503,013 B2
(45) Date of Patent: Jan. 7, 2003

(54) METHOD FOR APPLYING A MEDICAMENT AND SWAB APPLICATOR FOR USE THEREWITH

(75) Inventor: Richard Strauss, Woodbury, NY (US)

(73) Assignee: Pedinol Pharmacal Inc., Farmingdale, NY (US)

(*) Notice: Subject to any disclaimer, the term of this patent is extended or adjusted under 35 U.S.C. 154(b) by 0 days.

(21) Appl. No.: 09/975,825

(22) Filed: Oct. 11, 2001

(65) Prior Publication Data

US 2002/0044816 A1 Apr. 18, 2002

Related U.S. Application Data

(60) Provisional application No. 60/239,996, filed on Oct. 13, 2000.

(51) Int. Cl.[7] .............................................. A46B 11/00
(52) U.S. Cl. ........................ 401/123; 401/119; 401/125; 401/132; 401/133
(58) Field of Search ..................... 401/118–120, 123, 401/125, 132, 133; 118/264, 266; 222/205

(56) References Cited

U.S. PATENT DOCUMENTS

| | | | |
|---|---|---|---|
| 3,757,782 A | 9/1973 | Aiken | 128/269 |
| 3,792,699 A | 2/1974 | Tobin et al. | 128/2 W |
| 4,173,978 A | 11/1979 | Brown | 128/269 |
| 4,747,719 A * | 5/1988 | Parkin | 401/132 |
| 4,799,815 A | 1/1989 | Barabino et al. | 401/132 |
| 4,843,097 A * | 6/1989 | Shroot et al. | 514/680 |
| 4,875,602 A | 10/1989 | Chickering et al. | 222/187 |
| 6,186,971 B1 | 2/2001 | Naughton | 604/2 |
| 6,447,476 B1 * | 9/2002 | Sogaro | 604/85 |

FOREIGN PATENT DOCUMENTS

| WO | 00/38777 A1 | 7/2000 | A61M/35/00 |
|---|---|---|---|

OTHER PUBLICATIONS

Dentaco Catalog, Fall 1988 (3 pages).

\* cited by examiner

*Primary Examiner*—Gregory Huson
*Assistant Examiner*—Tuan Nguyen
(74) *Attorney, Agent, or Firm*—Darby & Darby

(57) ABSTRACT

A method of applying a medicament using a disposable swab applicator formed of a swab and a housing including a reservoir member and an adjustable sleeve member is provided. The reservoir member has a channel formed therein for receiving and storing the medicament with the adjustable inner sleeve member also being disposed within the channel. The inner sleeve member has an open first end which receives the swab and a closed second end with one or more windows formed between the first and second ends. In a first position within the reservoir member, the closed second end of the inner sleeve member forms a seal with the reservoir member to effectively store the medicament in the reservoir member. Movement of the inner sleeve member from the first position to a second position causes the medicament to flow through the one or more windows into contact with the swab resulting in the swab being ready for use.

5 Claims, 2 Drawing Sheets

METHOD FOR APPLYING A MEDICAMENT AND SWAB APPLICATOR FOR USE THEREWITH

CROSS-REFERENCE TO RELATED APPLICATION

This application claims the benefit of U.S. patent application Ser. No. 60/239,996, filed on Oct. 13, 2000, and which is incorporated herein by reference in its entirety.

TECHNICAL FIELD

The present invention relates to a method for applying a medicament and more particularly, relates to a method for applying a medicament using a disposable swab applicator which includes a self-contained medicament which is applied to the swab when the applicator is activated.

BACKGROUND OF THE INVENTION

Swab applicators have a wide array of uses and typically are formed of a cotton tipped swab, which is used to apply a medium, and a housing in which the swab and/or the medium are stored. Swab applicators find particular utility in the medical field where they are used in a variety of settings, including but not limited to applying topical antiseptics, cleansing skin surfaces, and removing cerumen from the ears, etc.

One type of swab applicator includes a cotton tipped swab which is sealed in a sterilized package and the medium to be applied is stored in a separate container, such as a bottle. To apply the medium to an intended application surface, the cotton tipped swab is removed from the package and the container is opened. The cotton tipped swab is then dipped and redipped into the medium so as to saturate the cotton tip of the swab. The cotton tip is then placed into contact with the application surface to effectuate a transfer of the medium to this surface. While these type of applicators are suitable for their intended use, they suffer from several disadvantages. The repeated dipping and redipping of cotton tipped swabs into the applicator medium provides an opportunity for the medium to be contaminated as the bottle is repeatedly opened and cotton tipped swabs are first dipped into the applicator medium and then placed in contact with the application surface before then being placed back into contact with the applicator medium. Accordingly, the redipping of the cotton tipped swab in the reservoir of applicator medium may result in the contamination of the applicator medium by foreign particles or spore forming bacteria being transferred from the applicator surface of the cotton tipped swab and then to the applicator medium.

In order to overcome the disadvantages associated with using a cotton tipped swab with an externally supplied applicator medium, applicator swabs have been designed so that a pre-measured amount of applicator medium is disposed within a compartment of the applicator unit itself. For example, the applicator medium is stored within a shaft of the swab itself and then upon activation of the applicator swab, the applicator medium is externally disposed through the shaft of the swab onto its absorbent cotton form and then onto the applicator surface.

In addition, other types of swab applicators have been used in which the swab applicators are of a pre-treated type. In these types of applicators, each cotton tipped swab is individually stored within its own housing such that the absorbent cotton tip of the swab is disposed within the applicator medium until the housing is separated to thereby free the pre-treated cotton tipped swab. The absorbent cotton tip is thus packaged and stored so that the absorbent cotton tip is saturated with the applicator medium and the user simply removes the applicator swab from the package and then breaks open the housing to free the saturated cotton tipped swab. The saturated cotton tip is then brought into contact with the applicator surface for transferring the applicator medium to the applicator surface. The advantage of this type of applicator is that it provides a very simplistic applicator unit which is easy to use and is disposable after use. However, one of the associated disadvantages is that over time the saturated cotton tip of the swab may dry out resulting in less applicator medium being applied to the applicator surface. The evaporation of the applicator medium and subsequent drying out of the cotton tip results if the seal between the housing and the cotton tipped swab is less than perfect. Many of the applicator mediums which are used in these types of applicators swabs easily evaporate if left exposed to atmospheric conditions for a period of time.

It is therefore desirable to provide a simple yet effective method for applying a medicament using an applicator swab device in which the medicament is self-contained within the device.

SUMMARY OF THE INVENTION

A method is provided for applying a medicament using a disposable swab applicator having a self-contained medicament that is stored and sealed within an ampoule housing. A swab is conveniently held and removably retained within the housing with an applicator end of the swab designed to apply the medicament.

The housing includes a reservoir member which has a channel formed therein for receiving a predetermined amount of the medicament along with an adjustable inner sleeve member. The adjustable inner sleeve member is disposed within the channel and receives the applicator end of the swab within a latitudinal opening formed in the inner sleeve member. One end of the inner sleeve member forms a seal with the reservoir member when the inner sleeve member is in a first position within the reservoir member. This first position is a storage position in which the medicament is stored in the channel of the reservoir member between the one end of the inner sleeve member and a closed end of the reservoir member.

To activate the swab applicator, the swab is directed downward causing the inner sleeve member to move from the sealed first position to a second position in which the applicator end of the swab communicates with the stored medicament. After a sufficient amount of medicament is disposed on the applicator end, the swab is removed from the housing with the inner sleeve member remaining retained within the reservoir member. The swab is then placed into contact with the area to be treated (e.g., tissue) so that the medicament is effectively transferred to this site.

Accordingly, a simple yet effective method is provided for applying a medicament using a disposable swab applicator. Because the medicament is stored in a sealed compartment separate from the swab, the applicator end of the swab does not dry out as is the case with many of the pre-treated swab applicator devices. The swab applicator is activated very simply by pushing the swab downward within the housing so that the inner sleeve member moves to the second position and the medicament flows onto the applicator end of the swab.

This type of swab applicator is particularly useful for applying a medicament to an area which is being treated by an individual, such as a doctor. For example, the swab applicator finds particular utility in applying medicament to an area from which an ingrown toenail has been removed. Furthermore, the present swab applicator may also be used for applying medicament to warts and the like. It will be understood that a number of other applications are contemplated besides the aforementioned.

Other features and advantages of the present invention will be apparent from the following detailed description when read in conjunction with the accompanying drawings.

BRIEF DESCRIPTION OF THE DRAWINGS

The foregoing and other features of one exemplary embodiment will be more readily apparent from the following detailed description and drawings of an illustrative embodiment in which.

DETAILED DESCRIPTION OF PREFERRED EMBODIMENTS

Figure 1:
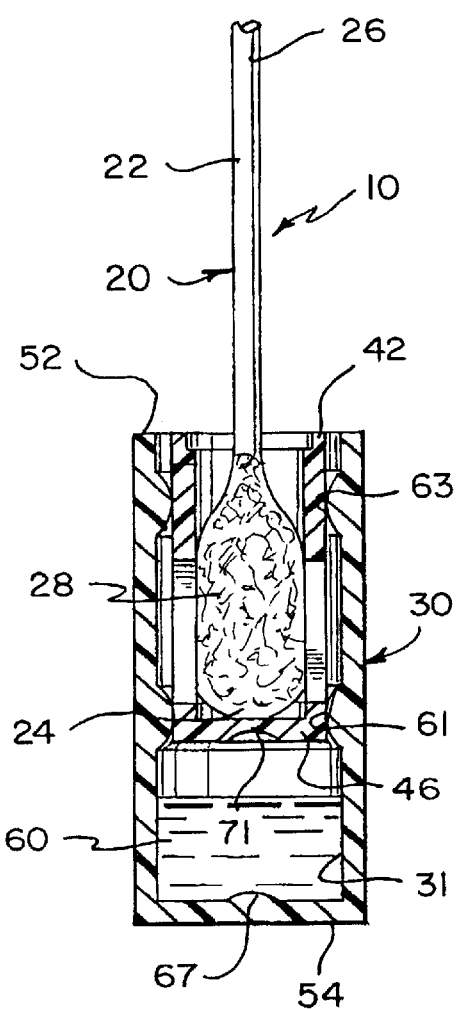
FIG. 1 is a cross-sectional view of one exemplary swab applicator in a first position.

Referring to FIGS. 1–4, a swab applicator for use according to the present invention is illustrated and indicated at 10. FIG. 1 shows the swab applicator 10 in a first position which is a pre-activation position. The swab applicator 10 is formed of a swab 20 and a housing assembly 30. The swab 20 includes a stem 22 having a first end 24 and an opposing second end 26. The stem 22 is made of any number of suitable materials, including but not limited to suitable plastics. Preferably, the stem 22 is of a solid type rather than being hollow. The second end 26 of the swab 20 is a free end which is intended to be gripped and manipulated by an individual during use of the swab applicator 10. The first end 24 of the swab 20 has an absorbent material 28 disposed thereat. The absorbent material 28 is of a known type, including but not limited to cotton fibers or synthetic fibers, such as plastic fibers. The absorbent material 28 is attached to the first end 24 of the swab 20 in a conventional manner.

Figure 3:
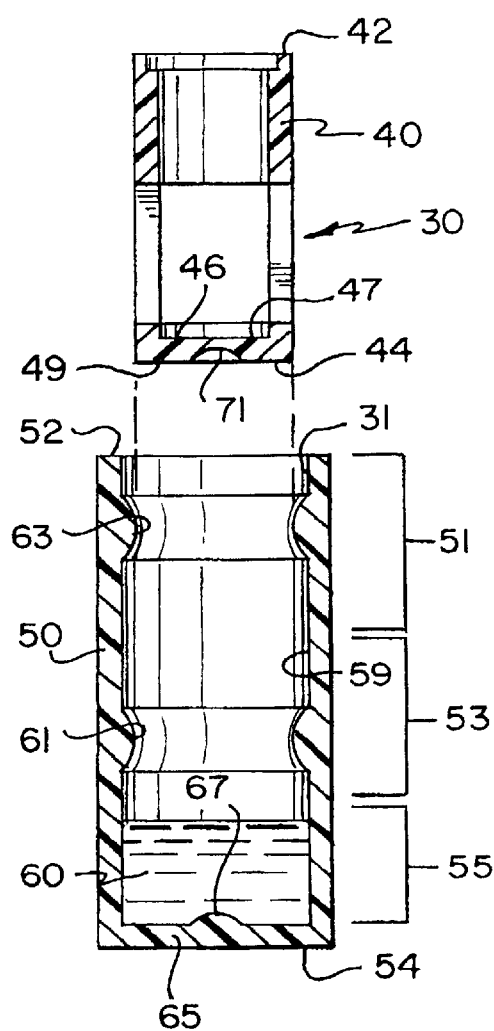
FIG. 3 is an exploded cross-sectional view of a housing assembly used in the applicator of FIG. 1.

As best shown in FIG. 3, the housing assembly 30 is of an ampoule type and includes an adjustable inner sleeve member 40 and a reservoir member 50. The reservoir member 50 comprises a receptacle for holding a predetermined amount of medicament, generally indicated at 60. In the exemplary embodiment, the reservoir member 50 has an annular shape and includes an open end 52 and an opposing closed end 54 with a channel 31 being formed therein from the open first end 52 to the closed end 54. According to the present invention, the reservoir member 50 has a varying inner diameter. As best shown in FIG. 3, the reservoir member 50 may be thought of as having a first section 51 terminating in the open end 52, a second section 53, and a third section 55 terminating in the closed end 54.

Each of the first and second sections 51, 53, respectively, includes a feature which is designed to create interference between the inner sleeve member 40 and the reservoir member 50. In one exemplary embodiment, this interference is created by reducing the inner diameter of the reservoir member 50 within each of the first and second sections 51, 53. In other words, an inner surface 59 of the reservoir member 50 includes two distinct annular bands 61, 63 formed on the inner surface 59 of the first and second sections 51, 53, respectively. These annular bands 61, 63 thus form annular necks within the channel 31 of the reservoir member 50 and are designed to create interference with the inner sleeve member 40 as a result of the inner sleeve member 40 having an outer diameter which is equal to or greater than the inner diameter of the annular necks 61, 63. The annular necks 61, 63 thus serve to locate and retain the inner sleeve member 40 in the first position as will be described hereinafter. Preferably, the inner diameter of the inner surface 59 surrounding the annular necks 61, 63 is approximately the same.

The inner diameter of all three sections 51, 53, 55 of the reservoir member 50 is greater than an outer diameter of the first end 24 contained in the inner sleeve member 40 of the swab 20 (defined by the absorbent material 28) so that the first end 24 may be received within the channel 31 formed in the reservoir member 50. The reservoir member 50 may be formed of any number of suitable materials, e.g., a plastic. Preferably, the reservoir member 50 is formed of a transparent material so that the medicament 60 may be viewed. This permits the user to immediately determine the presence of the medicament 60 and also determine the level of the medicament 60.

The closed second end 54 of the reservoir member 50 is formed by an annular disk-like member 65. Preferably, the disk-like member 65 has a slight protrusion 67 formed in a central section thereof for locating and mating with a complementary feature formed on the inner sleeve member 40. In the exemplary embodiment, the protrusion 67 is in the form of an annular bump formed in the central section of the disk-like member 65.

Figure 2:
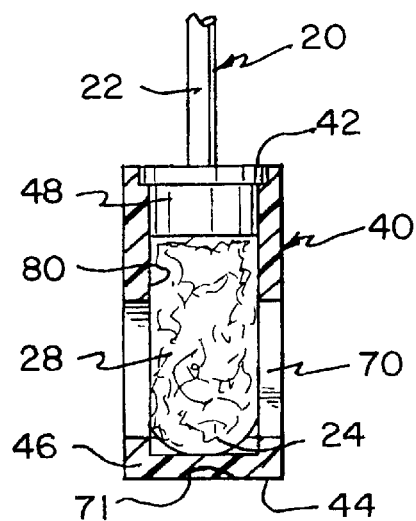
FIG. 2 is a side elevation view of a swab disposed in an inner sleeve member for use in the applicator of FIG. 1.

The inner sleeve member 40 is designed to seal the medicament 60 at the closed second end 54 of the reservoir member 50 and also provides a member for receiving and holding the first end 24 of the swab 20 during use of the swab applicator 10, as best shown in FIG. 2. The inner sleeve member 40 has an open first end 42 and an opposing closed second end 44. The inner sleeve member 40 has a complementary shape as the channel 31 of the reservoir member 50 so that the inner sleeve member 40 may be received within the reservoir member 50 and seal the medicament 60 therein. Therefore in the exemplary embodiment shown in FIG. 3, the inner sleeve member 40 has an annular shape. Preferably, the inner sleeve member 40 has a contrasting color compared to the reservoir member 50. This permits a more clearer delineation between the inner sleeve member 40 and the reservoir member 50 and also permits the compartment in which the medicament 60 is stored to be more easily viewed.

The closed second end 44 is formed by a disk member 46 which has a first surface 47 and an opposing second surface 49 which faces the medicament 60 when the inner sleeve member 40 is properly positioned within the reservoir member 50 (FIG. 1). The first surface 47 of the disk member 46 optionally has a slightly recessed platform (not shown) formed therein for receiving and locating the first end 24 of the swab 20. The outer diameter of the disk member 46 is less than the inner diameter of the inner surface 59 surrounding the annular necks 61, 63 of the reservoir member 50. The second surface 49 has a recess 71 formed therein which is complementary to and is designed to receive the protrusion 67 when the inner sleeve member 40 moves into the second position at the second end 54.

Referring to FIGS. 2 and 3, the first end 42 of the inner sleeve member 40 has an annular band 48 which provides structural support to the first end 42 of the inner sleeve member 40 with a channel 33 extending through the annular band 48. The annular band 48 has an inner diameter which is sized to receive the absorbent material 28 at the first end 24 of the swab 20. Preferably, the outer diameter of the first end 24 of the swab 20, defined by the absorbent material 28, is about equal to or slightly less than the inner diameter of the annular band 48 so that the first end 24 snugly fits between the inner sleeve member 40 as the swab 20 is inserted and removed from the inner sleeve member 40. The outer diameter of the annular band 48 is preferably about equal to or slightly greater than the outer diameter of the disk member 46 in one embodiment. Furthermore, the outer diameter of the annular band 48 is about equal to or slightly less than the inner diameter of the first section 51 of the reservoir member so that a frictional fit results therebetween when the inner sleeve member 40 is inserted.

Between the disk member 46 and the annular band 48, a pair of opposing connector legs 70 are provided for connecting the disk member 46 to the annular band 48. The connector legs 70 also provide structural support to the entire inner sleeve member 40. In one exemplary embodiment, the connector legs 70 are disposed approximately 180° apart from one another with each connector leg 70 having a generally rectangular shape. The connector legs 70 also serve to pinch and retain the first end 24 of the swab 20 when it is inserted therebetween. The inner sleeve member 40 also includes opposing latitudinal windows 80 defined by the connector legs 70, annular band 48, and the disk member 46. More specifically, each window 80 is formed between the spaced connector legs 70. Each of the exemplary latitudinal windows 80 has a generally rectangular shape and each is designed to permit the user to view the first end 24 of the swab 20 prior to and during activation of the swab applicator 10. Preferably, the inner sleeve member 40 comprises an integral molded member formed of a resilient plastic, e.g., an elastomer.

Referring especially to FIG. 1, the first position of the swab applicator 10 will now be described. In the first position, a predetermined amount of medicament 60 is disposed within the reservoir member 50 at the closed second end 54 thereof. The medicament 60 may comprise any number of materials which are to be applied to a surface. For example, the swab applicator 10 finds particular utility in medical applications in which the medicament 60 is a medicinal agent, such as an antiseptic or other treatment agent. In one exemplary use of the swab applicator 10 of the present invention, the medicament 60 is a phenol solution for use in podiatry and dermatology applications (described in greater detail hereinafter). More specifically, the medicament 60 is a liquid solution containing about 89% phenol by volume. In another use, the medicament 60 is a solution of monochloroaceticacid as will also be described hereinafter.

It will be appreciated that the medicament 60 may be disposed within the reservoir member 50 in a number of forms, including but not limited to a solid, a liquid, a paste, etc. When the medicament 60 is in the form of a liquid, the absorbent material 28 absorbs the liquid and when the medicament 60 is in a form other than a liquid, e.g., a gel, paste, or solid, the absorbent material acts as a carrier of the medicament 60. It will also be understood that the medicament 60 may be any number of mediums which are intended to be dispersed and applied using an instrument, such as swab 20.

After the predetermined amount of medicament 60 has been dispersed into the reservoir member 50, the inner sleeve member 40 is inserted into the reservoir member 50. In the first position shown in FIG. 1, the first end 42 of the inner sleeve member 40 aligns with or is slightly below the first end 52 of the reservoir member 50. Because the volume of the medicament 60 disposed within the reservoir member 50 is carefully selected and the length of the inner sleeve member 40 is defined, the second end 44 of the inner sleeve member 40 is positioned slightly above a top surface of the medicament 60 in the first position. In other words, when the inner sleeve member 40 is inserted into the reservoir member 50, the disk member 46 is disposed slightly above the medicament 60.

Referring to FIGS. 1 and 3, the inner sleeve member 40, and more specifically the disk member 46, provides a seal which effectively isolates the medicament 60 in a sealed environment. The seal is formed by the interference created between the disk member 46 and the annular neck 61 formed within the channel 31. Because the inner diameter of the annular neck 61 is less than the inner diameter of the inner surface 59 in the surrounding second and third sections 53, 55 and is less than the outer diameter of the disk member 46, the disk member 46 is compressed as it is directed downward and engages the annular neck 61. The disk member 46 along with the other portions of the inner sleeve member 40 are sufficiently resilient so as to permit this seal to be formed.

At the same time, a section of the outer surface of the inner sleeve member 40 proximate to the open first end 52 engages the other interference section of the reservoir member 50, namely the annular neck 63. The interference created between this section of the inner sleeve member 40 and the reservoir member 50 is designed to further position and retain the inner sleeve member 40 within the first position. This further ensures that the inner sleeve member 40 does not move prior to activation.

Preferably, when the first ends 42, 52 align, the second end 44 is disposed between the annular neck 61 in the second section 53 to produce the desired seal. This permits the swab applicator 10 to be stored for extended periods of time without the medicament 60 either leaking or evaporating from the reservoir member 50. The medicament 60 is prevented from flowing out of the compartment of the third section 57 of the reservoir member 50 and making contact with the swab 20 because the interference created at the annular neck 61 prevents the medicament 60 from flowing around the disk member 46.

In the first position, the first end 24 of the swab 20 is inserted within the annular band 48 and is directed downwardly between the connector legs 70 until the first end 24 rests within the recessed platform of the disk member 46. Because of the slight frictional fit between the first end 24 and the connector legs 70, the first end 24 is sufficiently retained within the inner sleeve member 40 such that if the swab applicator 10 is turned upside down, the swab 20 does not freely fall therefrom. In this first position, the swab 20 is not in contact with the medicament 60 to permit easy storage and transportation of the swab applicator 10. The swab applicator 10 will likely be individually packaged in a sealed package. The secure interference fit permits the swab applicator 10 to be inverted while still isolating the medicament 60 from the swab 20.

When an individual desires to use the swab applicator 10, the individual simply rips the package open and removes the swab applicator 10 from the package. To activate, the individual pushes the swab 20 downward causing the first end 24 to push the disk member 46 downward toward the closed second end 54. As the inner sleeve member 40 is pushed downward, the disk member 46 clears the annular neck 61 and enters the third section 55 where the channel 31 has a greater diameter due to the inner diameter of the third section 55 being greater than the inner diameter of the annular neck 61. This movement effectively removes the interference between the annular neck 61 and the disk member 46 of the inner sleeve member 40.

Figure 4:
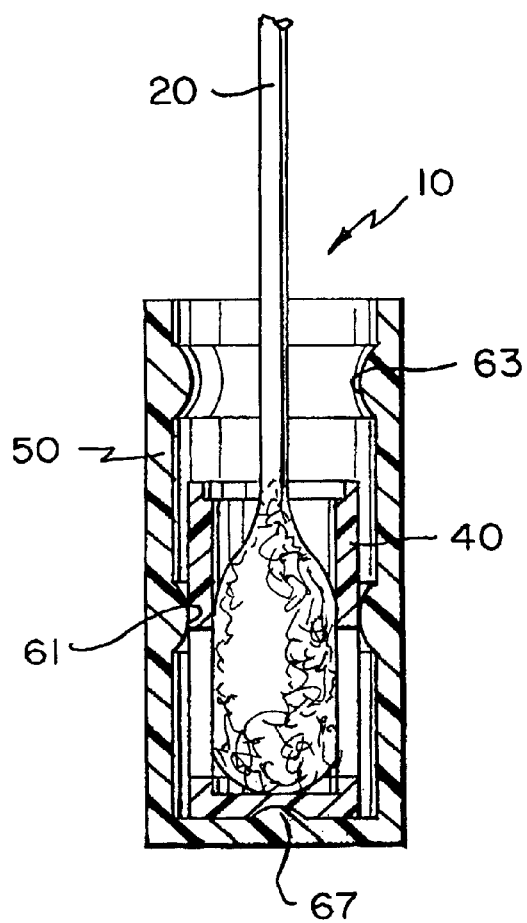
FIG. 4 is a cross-sectional view of the swab applicator of FIG. 1 in a second position in which the inner sleeve member has been punctured and the swab is contact with the medicament.

Due to its resilient nature, the disk member 46 slightly flexes outward after it clears the neck section 53 as it was previously in a compressed state. However, the outer diameter of the disk member 46 in the relaxed state is less than the inner diameter of the third section 55 and thus the pushing of the inner sleeve member 40 toward the closed second end 54 causes the medicament 60 to flow around the disk member 46, through the windows 80 and into contact with the second end 24 of the swab 20. This results in the absorbent material 28 of the swab 20 becoming saturated. In the case where the medicament 60 is in a gel, paste, or solid form, the movement of the inner sleeve member 40 causes the medicament 60 to come into contact with and be disposed on the absorbent material 28. This second position (post-activation position) of the swab applicator 10 is illustrated in FIG. 4. In this second position, the disk member 46 preferably seats against the closed second end 54 and a slight gap between the outer periphery of the disk member 46 and the inner surface 59 permits the medicament 60 to flow around the disk member 46.

In the second position, the protrusion 67 is received within the recess 71 so as to further locate and detachably retain the inner sleeve member 40 relative to the reservoir member 50.

Once saturated, the swab 20 is pulled from the inner sleeve member 40 in a saturated state and is ready for application to the application surface. The annular necks 61, 63 prevent the inner sleeve member 40 from being easily withdrawn from the reservoir member 50 as the swab 20 is removed because the inner sleeve member 40 is required to clear both annular necks 61, 63. In order to remove the inner sleeve member 40 completely from the reservoir member 50, the disk member 46 must be compressed again to fit between the annular necks 61, 63 and therefore the inner sleeve member 40 will not freely separate from the reservoir member 50 as the swab 20 is removed during normal use. After use, the swab applicator 10 is intended to be disposed of with other waste.

Figure 5:
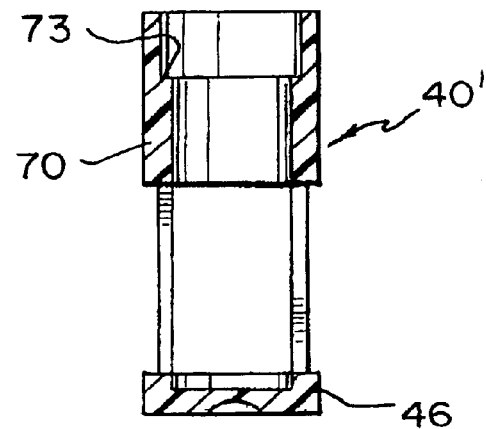
FIG. 5 is a cross-sectional view of another exemplary inner sleeve member for use in the applicator of FIG. 1.

FIG. 5 is a cross-sectional view showing another alternative embodiment of the inner sleeve member 40'. The sleeve member 40' includes the disk member 46 and connector legs 70 with the main difference being that member 40' has a stepped construction, generally indicated at 73, defined along its inner surface.

It will be understood that the present application in a broad sense covers a swab applicator 10 and a method of dispensing a medium (medicament 60) using the swab applicator 10 where the medium is initially sealed in a compartment by an interference formed between an adjustable member (inner sleeve member 40) within the reservoir member 50. The medicament 60 is dispensed by manipulating the adjustable member so that the interference is removed and the medicament 60 is permitted to flow into contact with the applicator instrument, in this case a swab 20. While, the exemplary embodiments shown herein provide the interference by using several annular neck sections 61, 63 formed in the channel 31 of the reservoir member 50, it will be appreciated by those skilled in the art that there are a number of different ways of creating this type of interference. The present swab applicator 10 is thus not limited to the described and illustrated method of forming the interference but rather covers other means for producing the desired interference.

The swab applicator 10 provides a simple yet effective disposable applicator which contains a self-contained medicament and is designed to overcome the disadvantages associated with conventional applicators and conventional application methods. Because the first end 24 of the swab 20 is not in contact with the medicament 60 during storage (the first position), the first end 24 will not dry out and the effective sealing of the medicament 60 within the reservoir member 50 eliminates or reduces the risk that the medicament 60 will leak or evaporate prior to activation and use of the swab applicator 10.

According to the present invention, the swab applicator 10 is used for applying the medicament 60 to a surface which is to be treated with the medicament 60. The swab applicator 10 permits an individual, such as a doctor, to easily and conveniently, apply the medicament 60. The doctor simply removes the swab applicator 10 from its package and then activates the applicator by pushing the swab 20 downward causing movement of the inner sleeve member 40 to the second position which results in the medicament 60 being applied to the swab 20. The following examples are merely exemplary uses of the swab applicator 10 for applying the medicament 60 to a surface to be treated and do not serve to limit the scope of the present invention.

EXAMPLE 1

One suitable use for the swab applicator 10 is for applying a medicament (medicament 60) during a surgical procedure in which an ingrown toenail or the like is removed. As is known, ingrown toenails are extremely painful to the patient and typically are removed by excising the ingrown portion of the toenail. During this procedure, the medicament 60 is typically used to treat the area where the excision has been made and the ingrown toenail removed. For this type of application, one type of suitable medicament 60 is a phenol solution which is applied directly to the excision area. During the operation, it is desirable for the doctor to be able to easily apply the phenol solution 60 to the infected area once the nail has been removed.

The swab applicator 10 provides the doctor with a device which permits the doctor to easily and effectively apply the medicament 60. After making the excision and removing the ingrown portion, the doctor removes the swab applicator 10 from the package and activates the applicator 10 by pressing the swab 20 downward causing the phenol solution 60 to come into contact with the swab 20. After the phenol solution 60 has been sufficiently absorbed by the swab 20, the swab 20 is removed and then placed into contact with the area to be treated so that the phenol solution 60 is applied to this area. The doctor may thoroughly treat this area using the swab 20. Phenol solution 60 is used because of its antiseptic properties and also because it acts as an oxidizing agent for treating the infected tissue to prevent regrowth of the toenail into the tissue. Due to its oxidizing properties, the phenol solution will slightly burn the tissue to prevent such regrowth.

EXAMPLE 2

Another suitable use for the swab applicator 10 is for applying a medicament (medicament 60) during a procedure in which a wart is treated. The more common areas where warts may grow are the hands and feet of a patient. Various types of warts may form on one or more of these regions along with other regions of the body. For example, some types of warts which commonly grow on a foot are plantar warts, mosaic warts, and multiple warts. One effective medicament 60 that is used in treating warts is a solution of monochloroaceticacid.

According to the present invention, the swab applicator 10 is used for treating one or more warts of the patient. In this application, the medicament 60 stored in the reservoir member 50 comprises a solution of monochloroaceticacid. After preparing the wart, the doctor removes the swab applicator 10 from the package and activates the applicator 10 by pressing the swab 20 downward causing the solution of monochloroaceticacid 60 to come into contact with the swab 20. After the monochloroaceticacid solution 60 has been sufficiently absorbed by the swab 20, the swab 20 is removed and then placed into contact with the area to be treated so that the monochloroaceticacid solution 60 is applied to the surface of the wart. The doctor may thoroughly treat the wart using the swab 20. After use, the swab applicator 10 is conveniently disposed of along with other medical waste.

In either application set forth in Examples 1 and 2, if all of the medicament 60 has not been initially absorbed by the swab 20, the doctor may place the first end 24 of the swab 20 back into the inner sleeve member 40 in its second position so that the first end 24 again contacts the medicament 60. Preferably, the doctor will not be required to do this as the applicator 10 is designed so that activation thereof causes the swab 20 to sufficiently absorb the medicament 60 so that the swab 20 contains a sufficient amount of medicament 60 for the application.

While the invention has been particularly shown and described with reference to the preferred embodiments thereof, it will be understood by those skilled in the art that various changes in form and detail may be made therein without departing from the spirit and scope of the present invention.

What is claimed is:

1. A method for applying a phenol solution to tissue surrounding an ingrown toenail, the method comprising:

providing a disposable swab applicator including a reservoir member holding the phenol solution and an adjustable inner sleeve member which receives a swab, the adjustable inner sleeve member being disposed in a first position in the reservoir member so that interference is formed between the inner sleeve member and the reservoir member, the interference effectively sealing the phenol solution in the reservoir member away from contact with the swab;

excising the ingrown toenail; and treating tissue surrounding the excised ingrown toenail by applying the phenol solution to the tissue, the treating of the tissue including:

adjusting the inner sleeve member to a second position within the reservoir member so that the interference is removed and the phenol solution freely communicates with the swab, thereby preparing the swab for use;

withdrawing the swab from the inner sleeve member; and applying the phenol solution to the tissue by contacting the tissue with the swab.

2. The method of claim 1, wherein the interference is created by providing a first band along an inner surface of the reservoir member, the first band being formed above the stored medium, the first band having an inner diameter that is less than an outer diameter of the adjustable sleeve member so that in the first position, the inner sleeve member is disposed between the first band to produce the interference and seal the medium from the swab.

3. The method of claim 2, wherein the interference is removed by moving the inner sleeve member to the second position where a portion of the inner sleeve member clears the first band, the portion of the inner sleeve member containing a window which permits the medium to freely communicate therethrough and into contact with the swab.

4. The method of claim 2, further including:

forming a second band along the inner surface of the reservoir member, the second band being remotely located relative to the medium such that the first band is formed between the medicament and the second band, wherein in the first position, an interference fit results between the first and second bands and the inner sleeve member, while in the second position, an interference fit results between only the first band and the inner sleeve member.

5. The method of claim 1, wherein the adjustment of the inner sleeve member from the first position to the second position causes a window formed in a side wall of the inner sleeve member to open relative to a compartment where the medium is stored, thereby permitting the medium to freely communicate through the window and into contact with the swab.

* * * * *